US011690668B2

(12) United States Patent
Wang et al.

(10) Patent No.: US 11,690,668 B2
(45) Date of Patent: Jul. 4, 2023

(54) COOLED RADIOFREQUENCY ABLATION PROBE

(71) Applicant: Avent, Inc., Alpharetta, GA (US)

(72) Inventors: Ruoya Wang, Decatur, GA (US); Ryan Smith, Atlanta, GA (US); Scott M. Teixeira, Cumming, GA (US); Craig F. Steinman, Cumming, GA (US); Ken Driver, Brookhaven, GA (US); Samir Merchant, Cumming, GA (US)

(73) Assignee: Avent, Inc., Alpharetta, GA (US)

( * ) Notice: Subject to any disclaimer, the term of this patent is extended or adjusted under 35 U.S.C. 154(b) by 529 days.

(21) Appl. No.: 16/229,098

(22) Filed: Dec. 21, 2018

(65) Prior Publication Data

US 2020/0197084 A1    Jun. 25, 2020

(51) Int. Cl.
*A61B 18/12* (2006.01)
*A61B 18/14* (2006.01)
*A61B 18/00* (2006.01)

(52) U.S. Cl.
CPC ...... *A61B 18/1492* (2013.01); *A61B 18/1206* (2013.01); *A61B 2018/00023* (2013.01);
(Continued)

(58) Field of Classification Search
CPC ............ A61B 18/1492; A61B 19/1206; A61B 18/148; A61B 2018/00577;
(Continued)

(56) References Cited

U.S. PATENT DOCUMENTS 6,241,722 B1 * 6/2001 Dobak .................. A61B 18/02
606/23
8,632,537 B2 * 1/2014 McNall, III ....... A61B 18/1485
606/47
(Continued)

FOREIGN PATENT DOCUMENTS

EP    1 600 113 A2    11/2005
EP    2 942 023 A2    11/2015
(Continued)

OTHER PUBLICATIONS

International Search Report and Written Opinion for PCT/US2019/066689, dated Mar. 31, 2020, 10 pages.

*Primary Examiner* — Daniel W Fowler
*Assistant Examiner* — Annie L Shoulders
(74) *Attorney, Agent, or Firm* — Meunier Carlin & Curfman LLC

(57) ABSTRACT

A cooling radiofrequency ablation probe for delivering electrical and thermal energy to tissue of a patient's body is provided. The probe comprises a handle having an upper portion, a lower portion, and a Luer connector. The probe further comprises an extended electrocap assembly interfacing with one end of the handle, and a cable-tubing assembly interfacing with another end of the handle. The cable-tubing assembly includes an electrical cable that terminates at an electrical connector and a dual-lumen fluid tubing that terminates at inlet and outlet fluid connectors. An active tip of the extended electrocap assembly is configured to deliver the electrical and thermal energy to the tissue of the patient's body.

22 Claims, 9 Drawing Sheets

(52) U.S. Cl.
CPC ......... *A61B 2018/00083* (2013.01); *A61B 2018/00577* (2013.01); *A61B 2018/00702* (2013.01); *A61B 2018/00791* (2013.01); *A61B 2018/00827* (2013.01); *A61B 2018/00964* (2013.01); *A61B 2018/126* (2013.01); *A61B 2018/1253* (2013.01)

(58) Field of Classification Search
CPC .......... A61B 2018/00023; A61B 2018/00083; A61B 2018/00964; A61B 2018/00172; A61B 2018/00339; A61B 2018/0044; A61B 2018/0091; A61B 2018/00994; A61B 2018/00821; A61B 18/1482
See application file for complete search history.

(56) References Cited

U.S. PATENT DOCUMENTS

| | | | |
|---|---|---|---|
| 9,956,032 B1 | 5/2018 | Cosman et al. | |
| 10,631,915 B1 * | 4/2020 | Cosman | A61B 18/14 |
| 2005/0177209 A1 | 8/2005 | Leung et al. | |
| 2010/0198066 A1 * | 8/2010 | Voegele | A61B 8/0841 606/33 |
| 2011/0295242 A1 * | 12/2011 | Spivey | A61B 17/320016 606/1 |
| 2013/0041369 A1 * | 2/2013 | Godara | A61B 18/1482 606/34 |
| 2014/0259641 A1 * | 9/2014 | Brannan | A61B 18/1815 29/602.1 |
| 2017/0202605 A1 * | 7/2017 | Shelton, IV | A61B 17/320068 |
| 2017/0245930 A1 * | 8/2017 | Brannan | A61B 18/1815 |
| 2017/0265882 A1 * | 9/2017 | Austria | A61B 17/3211 |
| 2018/0353234 A1 * | 12/2018 | Rooks | A61B 18/1402 |
| 2020/0121384 A1 * | 4/2020 | Mark | A61B 18/148 |

FOREIGN PATENT DOCUMENTS

| | | | | |
|---|---|---|---|---|
| WO | WO 94/26186 A1 | 11/1994 | | |
| WO | WO-9426186 A1 * | 11/1994 | ......... | A61B 18/1485 |
| WO | WO 99/35983 A1 | 7/1999 | | |
| WO | WO-9935983 A1 * | 7/1999 | ......... | A61B 18/1485 |
| WO | WO 02/28475 A1 | 4/2002 | | |
| WO | WO-0228475 A1 * | 4/2002 | ............. | A61N 1/06 |
| WO | WO 2013/016588 A1 | 1/2013 | | |

* cited by examiner

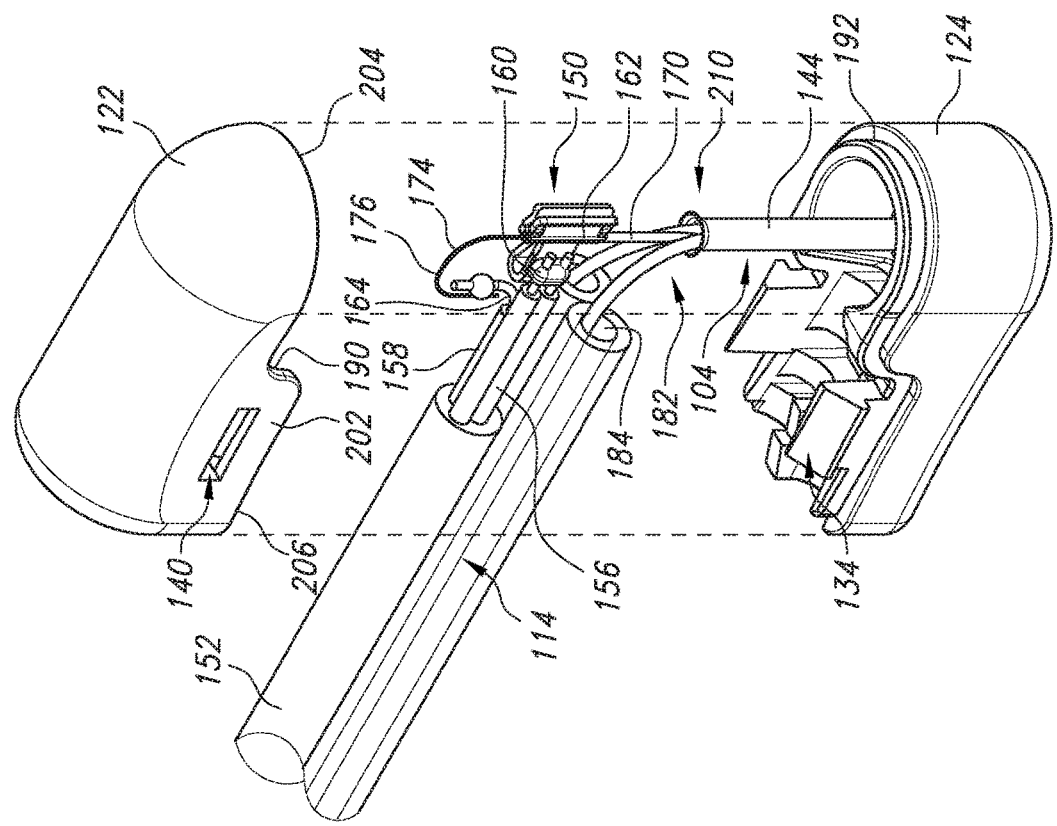

COOLED RADIOFREQUENCY ABLATION PROBE

FIELD OF THE INVENTION

The present invention relates generally to a system for applying energy for the treatment of tissue, and more particularly to a cooled radiofrequency probe having an optimized shape and size to improve handling and manipulation of the probe and minimize manufacturing complexity.

BACKGROUND

Lower back injuries and chronic joint pain are major health problems resulting not only in debilitating conditions for the patient, but also in the consumption of a large proportion of funds allocated for health care, social assistance and disability programs. In the lower back, disc abnormalities and pain may result from trauma, repetitive use in the workplace, metabolic disorders, inherited proclivity, and/or aging. The existence of adjacent nerve structures and innervation of the disc are very important issues in respect to patient treatment for back pain. In joints, osteoarthritis is the most common form of arthritis pain and occurs when the protective cartilage on the ends of bones wears down over time.

A minimally invasive technique of delivering high-frequency electrical current has been shown to relieve localized pain in many patients. Generally, the high-frequency current used for such procedures is in the radiofrequency (RF) range, i.e. between 100 kHz and 1 GHz and more specifically between 300-600 kHz. The RF electrical current is typically delivered from a generator via connected electrodes that are placed in a patient's body, in a region of tissue that contains a neural structure suspected of transmitting pain signals to the brain. The electrodes generally include an insulated shaft with an exposed conductive tip to deliver the radiofrequency electrical current. Tissue resistance to the current causes heating of tissue adjacent resulting in the coagulation of cells (at a temperature of approximately 45° C. for small unmyelinated nerve structures) and the formation of a lesion that effectively denervates the neural structure in question. Denervation refers to a procedure whereby the ability of a neural structure to transmit signals is affected in some way and usually results in the complete inability of a neural structure to transmit signals, thus removing the pain sensations. This procedure may be done in a monopolar mode where a second dispersive electrode with a large surface area is placed on the surface of a patient's body to complete the circuit, or in a bipolar mode where a second radiofrequency electrode is placed at the treatment site. In a bipolar procedure, the current is preferentially concentrated between the two electrodes.

To extend the size of a lesion, radiofrequency treatment may be applied in conjunction with a cooling mechanism, whereby a cooling means is used to reduce the temperature of the electrode-tissue interface. By cooling the probe, the tissue temperature near the probe is moderately controlled. In turn, more power can be applied to the target tissue without causing an unwanted increase in local tissue temperature that can result in tissue desiccation, charring, or steam formation. The application of a higher power allows regions of tissue further away from the energy delivery device to reach a temperature at which a lesion can form, thus increasing the size/volume of the lesion.

The treatment of pain using high-frequency electrical current has been applied successfully to various regions of patients' bodies suspected of contributing to chronic pain sensations. For example, with respect to back pain, which affects millions of individuals every year, high-frequency electrical treatment has been applied to several tissues, including intervertebral discs, facet joints, sacroiliac joints as well as the vertebrae themselves (in a process known as intraosseous denervation). In addition to creating lesions in neural structures, application of radiofrequency energy has also been used to treat tumors throughout the body. Further, with respect to knee pain, which also affects millions of individuals every year, high-frequency electrical treatment has been applied to several tissues, including, for example, the ligaments, muscles, tendons, and menisci.

Due to the large volume lesions generated by cooled radiofrequency ablation procedures, care must be taken when treating sensitive locations, particularly around areas that cannot sustain significant collateral ablative damage. Furthermore, existing cooled radiofrequency probes are often top-heavy and may impart a large torque about the probe insertion point due to the mass of the probe handle and the rigidity of the tubing and cable that are connected to the probe. FIG. 1 illustrates an existing cooled radiofrequency probe having an elongated cylindrical handle 10 which extends generally parallel to an elongated electrocap assembly 104. FIG. 2 illustrates a cross-sectional view of the interior components of the handle 10. This configuration extends the distance from which the probe assembly, including the electrocap assembly 104, the handle 10, and the electrical and fluid tubing extending from the handle 10, extends away from the patient's tissue, resulting in a large moment arm and the possibility of imparting a large torque about the probe insertion point. As a result, the existing cooled RF probes are often unwieldy and difficult to manipulate, thereby increase the risk of improper insertion and tissue injury at the probe insertion site.

Moreover, the existing cooled radiofrequency probes are difficult to manufacture, requiring intense processes requiring long assembly cycle times including many welds and solder joints and multiple long-duration curing stages of long-cure epoxy adhesives. The manufacturing difficulty of the existing cooled RF probes thereby results in high cost to manufacture.

Thus, the art is continuously seeking new and improved systems and methods for treating chronic pain using cooled RF ablation techniques, and more particularly to improved cooled radiofrequency probes having optimized shape and size to improve handling and ease manipulation of the probe and minimize manufacturing complexity.

SUMMARY OF THE INVENTION

The present invention provides a probe for delivering electrical and thermal energy to tissue of a patient's body. The probe includes: a handle having an upper portion and a lower portion generally extending in a longitudinal direction; an extended electrocap assembly interfacing with one end of the handle; and a cable-tubing assembly interfacing with another end of the handle, the cable-tubing assembly including an electrical cable that terminates at an electrical connector and a dual-lumen fluid tubing that terminates in inlet and outlet fluid connectors. The cable-tubing assembly extends from the handle at an angle of greater than 0 degrees and less than 180 degrees relative to the extended electrocap assembly.

In one particular embodiment, the handle can form a housing for electrical connection between the extended electrocap assembly and the electrical cable. Moreover, the probe can further include a clip positioned inside the handle, wherein the clip is configured to connect the electrical cable with the extended electrocap assembly.

In another embodiment, the handle can form a housing for fluid connection between the extended electrocap assembly and the dual-lumen fluid tubing.

In yet another embodiment, the lower portion can include a protrusion extending at an angle with respect to the longitudinal direction, wherein the extended electrocap assembly extends from the protrusion. Moreover, the angle can be in a range from about 45 degrees to about 135 degrees. Further, the protrusion can be generally perpendicular to the longitudinal direction.

In still another embodiment, the upper portion of the handle can include an upper shell, the lower portion of the handle can include a lower shell, and the upper shell and lower shell can be removably mated. Moreover, the removable mating between the upper shell and the lower shell can be configured to lock the upper shell and the lower shell together. Further, the removable mating between the upper shell and the lower shell can include at least one cantilevered snap on the lower shell configured to lock into a slot on the upper shell. Moreover, an inner perimeter of the upper shell can form a mating surface with an outer perimeter of the lower shell.

In one more embodiment, the electrocap assembly can have a handle end, and a distal end away from the handle, wherein the distal end can form an active tip for delivering electrical and thermal energy to tissue of the patient's body. Moreover, the handle end of the electrocap assembly can be configured to be positioned within the handle and to protrude from a hub of the handle. Further, the distal end of the electrocap assembly can extend in a direction generally perpendicular to the cable-tubing assembly. Moreover, a connection between a flared end of the handle end of the electrocap assembly and the handle can set the length of an elongate member of the electrocap assembly extending from the handle. Further, the handle end of the electrocap assembly can be flared. Moreover, an interference fit can secure the handle end of the electrocap assembly. Further, the active tip can be electrically and thermally conductive. Moreover, the electrocap assembly can include fluid tubing for carrying a cooling fluid to and from the active tip.

In yet another embodiment, the electrocap assembly can include a thermocouple hypotube made of a conductive material, wherein the thermocouple hypotube is operable to transmit energy from the electrical cable to an active tip of the probe, wherein the active tip can include a thermocouple to deliver electrical or radiofrequency energy to the patient tissue. Further, the thermocouple can protrude from a tip end of the extended electrocap.

In still another embodiment, the electrical cable and the dual-lumen fluid tubing can be bonded together along at least a portion of the length of the cable-tubing assembly. Further, the electrical cable and the dual-lumen fluid tubing can be not bonded at an end of the cable-tubing assembly adjacent to the electrical connector and fluid inlet and outlet connectors.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 7 illustrates an exploded view of the probe handle of FIG. 3;

DETAILED DESCRIPTION OF THE INVENTION

Figure 1:
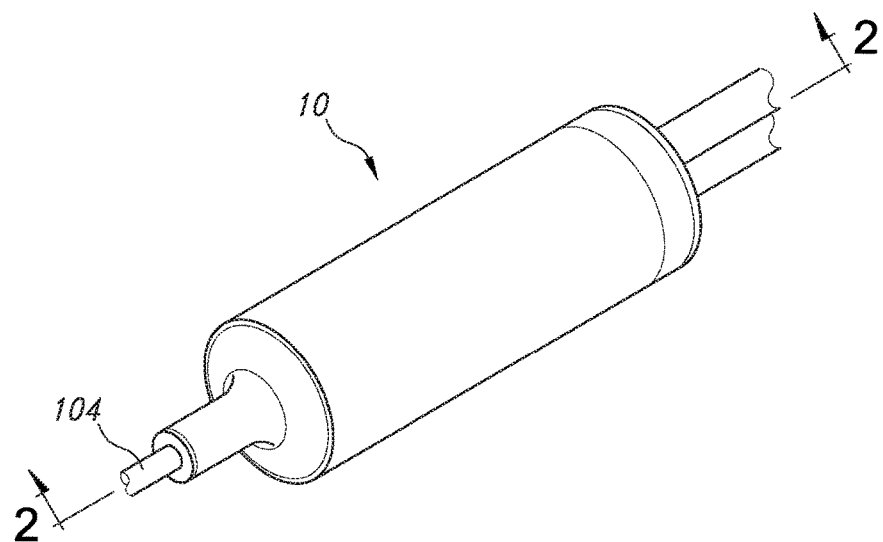
FIG. 1 illustrates a perspective view of a prior art cooled RF probe handle.

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

For the purposes of this invention, a lesion refers to the region of tissue that has been irreversibly damaged as a result of the application of thermal energy, and the invention is not intended to be limited in this regard. Furthermore, for the purposes of this description, proximal generally indicates that portion of a device or system next to or nearer to a handle of the probe (when the device is in use), while the term distal generally indicates a portion further away from the handle of the probe (when the device is in use).

As used herein, the terms "about," "approximately," or "generally," when used to modify a value, indicates that the value can be raised or lowered by 5% and remain within the disclosed embodiment.

Figure 3:
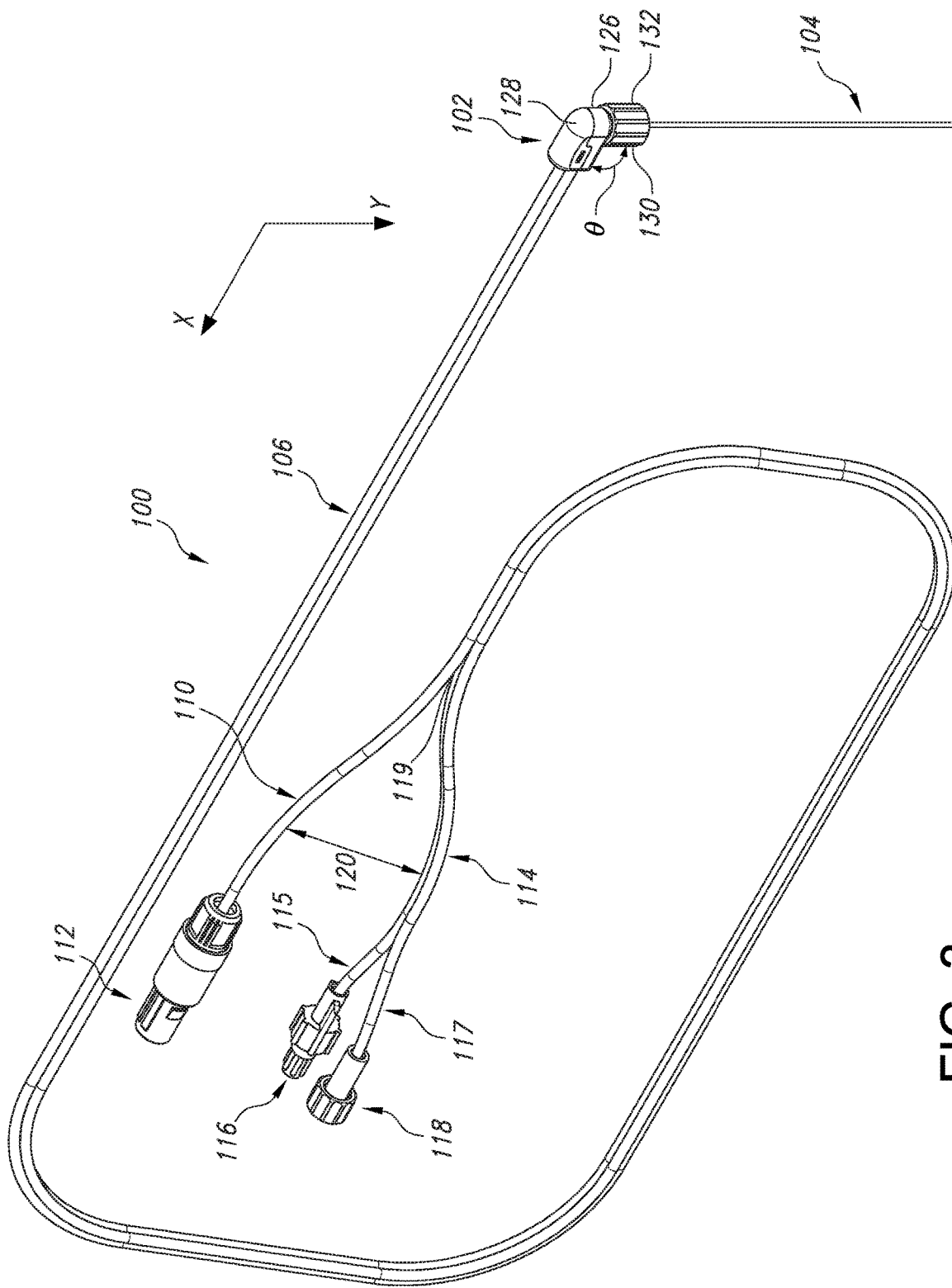
FIG. 3 illustrates a perspective view of a cooled RF probe assembly of an embodiment of the present invention including a probe handle.

Referring now to the drawings, FIG. 3 illustrates a cooled radiofrequency probe 100 of the present invention. As shown, the probe 100 includes a handle 102, an extended electrocap assembly 104, and a cable-tubing assembly 106. The handle 102 comprises an upper portion 128 and a lower portion 126 generally extending in a longitudinal x direction. The cable-tubing assembly 106 can communicate with the handle 102 at one end of the upper portion 128 and lower portion 126. The extended electrocap assembly 104 can communicate with the handle 102 at the lower portion 126. The lower portion 126 can include a distal protrusion 130 including a connector 132 and a hub 142 (shown in FIG. 4 and described in more detail below). The distal protrusion 130 can extend away from the longitudinal direction of the lower portion 126 at an angle θ that is greater than 0 degrees and less than 180 degrees. For instance, the angle θ can be in a range from about 45 degrees to about 135 degrees, such as from 60 to about 120 degrees. In one particular embodiment contemplated by FIG. 3, the angle θ may be about 90 degrees such that the distal protrusion 130 is oriented generally perpendicular to the longitudinal direction of the lower portion 126. The connector 132 on the distal protrusion 130 can be a Luer connector 132. The Luer connector 132 can lock the extended electrocap assembly 104 in place with a probe introducer (not shown) having a mating Luer connector. For example, the Luer connector 132 of the handle 102 can be a female Luer connector that is configured to receive a mating male Luer connector of a probe introducer.

As shown in FIG. 3, the cable-tubing assembly 106 includes an electrical cable 110 and a dual-lumen fluid tubing 114. The electrical cable 110 can include an insulating jacket 152 constructed from, for example, polyvinyl chloride (PVC) or any other suitable material. The electrical cable 110 can terminate at a proximal end at an electrical connector 112. The electrical connector 112 can be, for example, a circular electrical connector as shown in FIG. 3. The dual-lumen fluid tubing 114 can be constructed from two lumens 115 and 117 having walls constructed from clear polyvinyl chloride (PVC). The walls of the two lumens 115 and 117 can be thermally bonded together. The dual-lumen fluid tubing 114 can terminate at a proximal end at Luer connector 116 of lumen 115 and Luer connector 118 of lumen 117. Luer connector 116 can be positioned at the proximal end of lumen 115 and Luer connector 118 can be positioned at the proximal end of lumen 117. For example, lumen 115 can be an inlet fluid lumen with Luer connector 116 functioning as an inlet fluid connector, and lumen 117 can be an outlet fluid lumen with Luer connector 118 functioning as an outlet fluid connector. In one embodiment, Luer connector 116 can be a male Luer connector and Luer connector 118 can be a female Luer connector. Additionally, caps, e.g. vented caps, can be provided to cover or seal the Luer connectors 116 and 118 (not shown). The caps can be made from nylon or other suitable material and can have a different color or opacity than the Luer connectors 116 and 118.

The cable-tubing assembly 106 can be flexible due to the flexible materials of the insulating jacket 152 and the walls of the lumens 115 and 117. The cable-tubing assembly 106 can be bonded between the insulating jacket 152 of the electrical cable 110 and the wall of at least one of the lumens of the dual-lumen fluid tubing 114 along the length of the assembly 106. The bonding can be done, for example, by heat welding, UV adhesive, or any other suitable form of welding or bonding plastic or polymeric materials together. In one embodiment, the walls of the lumens 115 and 117 of the dual-lumen fluid tubing 114 can be bonded such that the lumens 115 and 117 extend side-by-side in parallel extending in a horizontal plane, as shown in FIG. 3. In one particular embodiment, the insulating jacket 152 of the electrical cable 110 can be bonded to the walls of both lumens 115 and 117. For example, the electrical cable 110 can be disposed in a recess 119 between the walls of the two lumens 115 and 117, as illustrated in FIG. 3. The cable-tubing assembly 106 can include at least one unbonded region 120 on the proximal connector end of the cable-tubing assembly 106 in which the electrical cable 110 and the dual-lumen fluid tubing 114 are not bonded together. The unbonded region may encompass a length of from about 6 inches to about 18 inches of the cable-tubing assembly 106, such as from about 8 inches to about 16 inches, such as from about 10 inches to about 14 inches. In one particular embodiment, the unbonded region may be about 12 inches. The lumens 115 and 117 of the dual-lumen fluid tubing 114 may remain bonded together for at least a portion of the unbonded region 120, as illustrated in FIG. 3. Alternatively, the lumens 115 and 117 of the dual-lumen fluid tubing 114 may be unbonded in the unbonded region 120.

Figure 5:
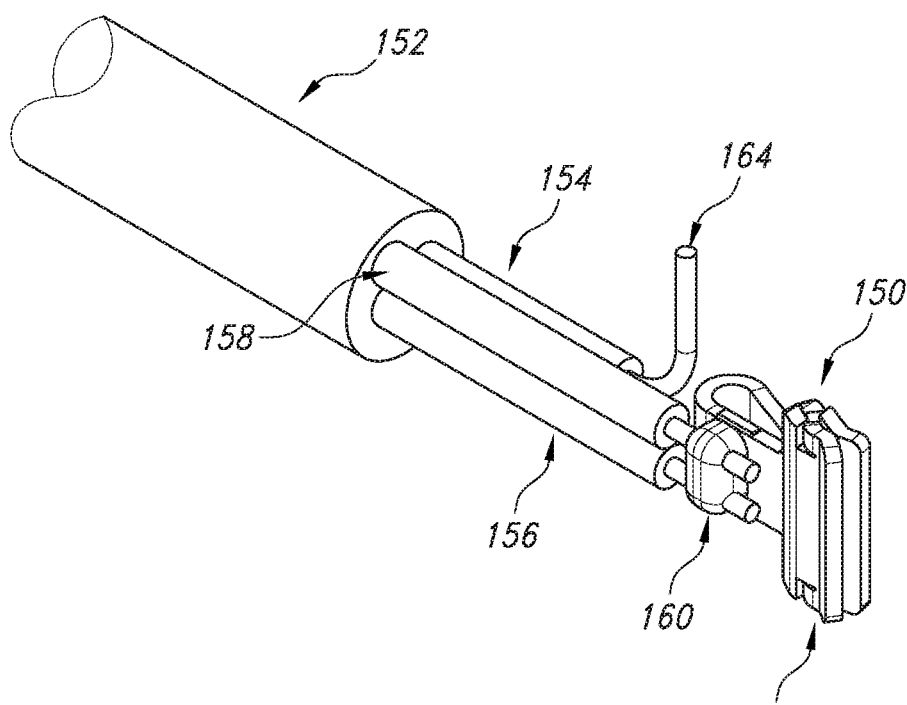
FIG. 5 illustrates a perspective view of an electrocable interconnect assembly of the electrical cable of the present invention.
Figure 6A:
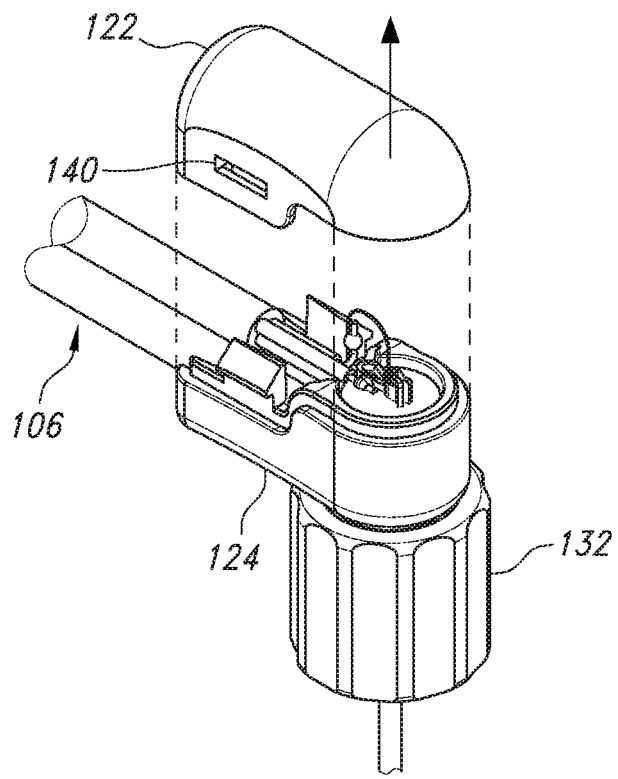
FIG. 6A illustrates an exploded view of a probe handle of the present invention.
Figure 6B:
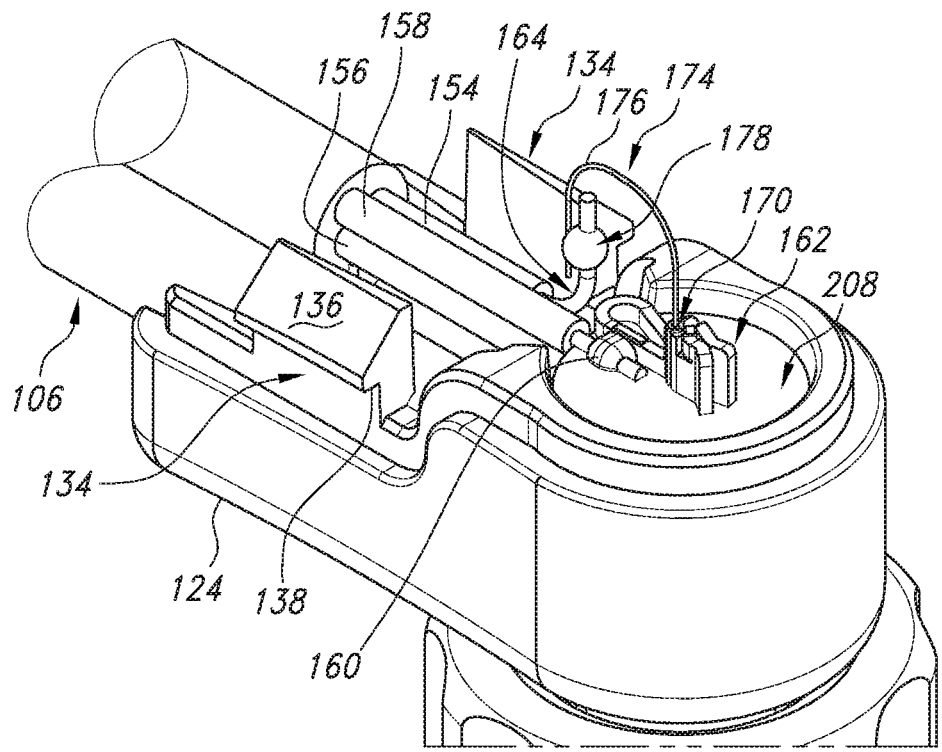
FIG. 6B illustrates a perspective view of the probe handle of FIG. 6A with the upper shell removed.

As shown in FIG. 5, the electrical cable 110 includes an electrical cable ("electrocable") interconnect 150 configured to be located within the handle 102. The insulating jacket 152 surrounds a first wire 154, a second wire 156, and a third wire 158. The first wire 154, second wire 156, and third wire 158 advantageously can have different colored insulating jackets so that the wires can be easily distinguished from one another. In one particular embodiment, the first wire 154 can have a red-colored insulated coating, the second wire 156 can have a blue-colored insulated coating, and the third wire 158 can have a green-colored insulated coating, although in other embodiments the colors of each of the wires can vary. The insulating jacket 152 may be directly extruded over the first wire 154, second wire 156, and third wire 158. The first wire 154 can include a conductor material made of constantan and is 28-gauge stranded. The second wire 156 and the third wire 158 each can include a conductor made of copper and are 28-gauge stranded. The second wire 156 and third wire 158 can be soldered at a solder joint 160 to a mechanical clip 162. Thus, the use of the mechanical clip 162 can reduce the number of solder joints necessary to electrically and/or mechanically couple the second wire 156 and third wire 158, improving the ease of manufacture. The free end 164 of the first wire 154 positioned within the handle 102 can be stripped free of insulating material, thereby leaving a section of conductor material exposed. FIGS. 6A and 6B further illustrate the electrocable interconnect 150 positioned in the interior of the handle 102.

Figure 8:
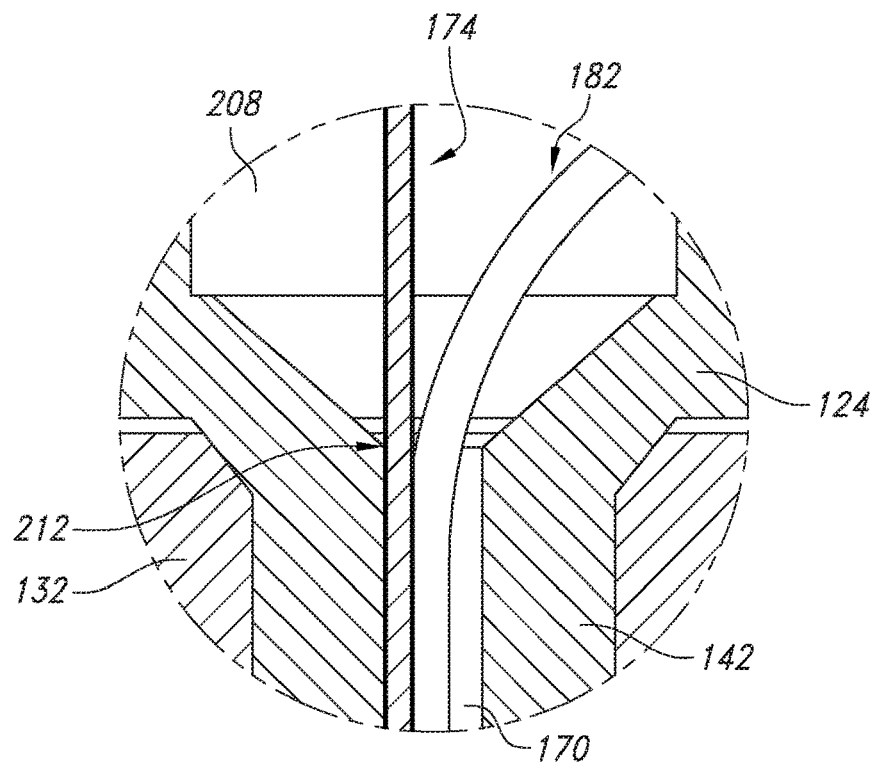
FIG. 8 illustrates a cut-away cross-sectional view of the lower shell and hub of the probe handle of FIG. 3.

Referring now to FIGS. 7-8, an exploded view of the handle 102 interior illustrating the interior components in the handle 102 and a cut-away cross-sectional view of the handle 102 interior are shown. When assembled, the mechanical clip 162 interfaces with the thermocouple hypotube 170 to provide a structurally and electrically sound connection. In one embodiment, the mechanical clip 162 may be clipped around a circumference of the hypotube 170. The mechanical clip 162 can surround an entire circumference of the hypotube 170. Thus, the mechanical clip 162 can mechanically connect the electrical wires 154, 156, 158 with the hypotube 170 by holding them in place within the handle interior. The thermocouple hypotube 170 can include a solid core constantan wire 174 having an end 176 protruding from the hypotube 170 into the handle 102 interior. The end 176 of the constantan wire 174 of the thermocouple hypotube 170 can be soldered to the free end 164 of the red wire 154 at solder joint 178 within the interior of the handle 102 adjacent to the clip 162. An adhesive material (not shown) may be used to encapsulate the components within the interior of the handle 102. In one embodiment, the adhesive material may be a UV cured adhesive.

Figure 4:
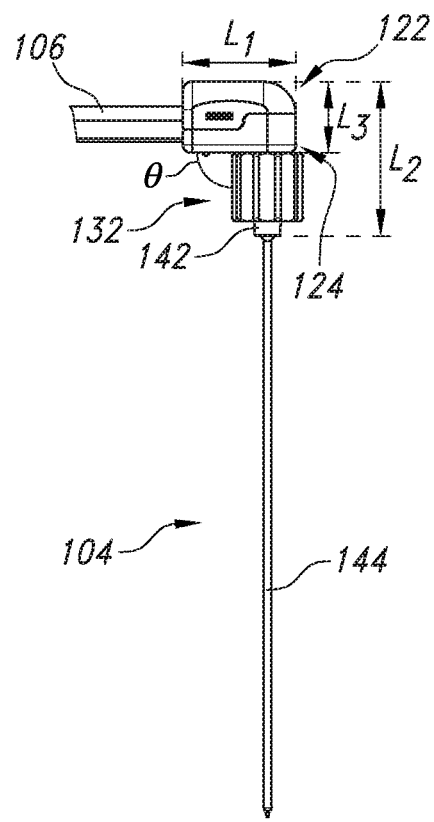
FIG. 4 illustrates a side view of the cooled RF probe assembly of FIG. 3.
Figure 9:
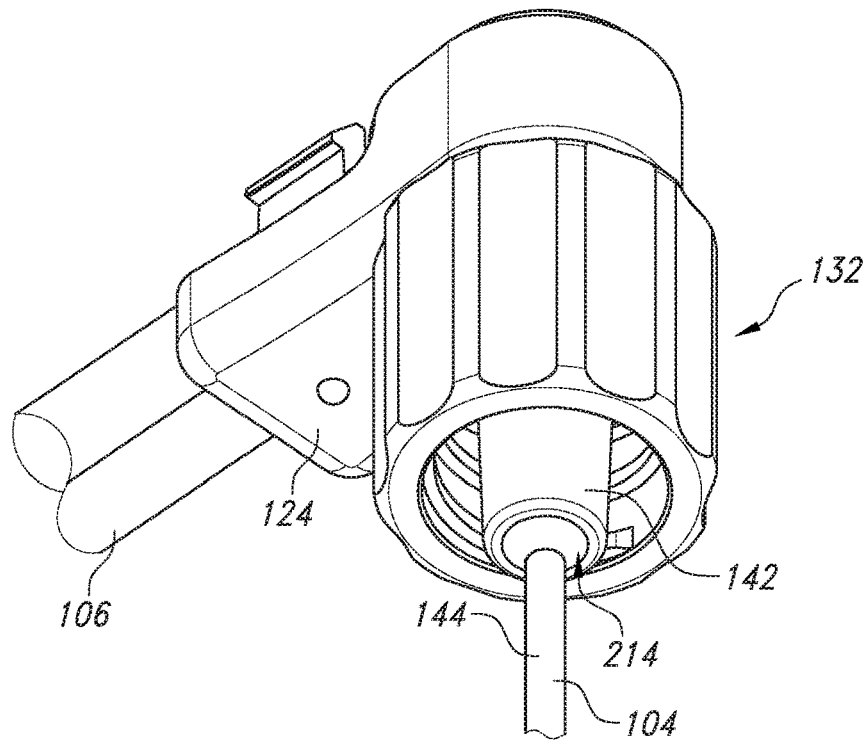
FIG. 9 illustrates a bottom perspective view of the probe of FIG. 3.

Turning now to FIGS. 4, 6B and 7, the electrocap assembly 104 includes an elongated tube 144 that is configured to protrude from the distal protrusion 130 of the handle 102 and extend continuously to the distal tip 220 of the electrocap assembly 104 (described in further detail below). As shown in FIGS. 6B and 7, a handle end 210 of the elongated tube 144 of the electrocap assembly 104 is configured to fit into a cavity 208 within a hub 142 of the distal protrusion 130 on the lower portion 126 of the handle 102. In one embodiment, the cavity 208 may be circular shaped. The handle end 210 of the electrocap assembly may be flared in order to fit into the cavity 208. The connection between the cavity 208 and the handle end 210 may be an interference fit 212 (see FIG. 8). The overall length of the elongated member 144 of the electrocap assembly 104 protruding from the distal protrusion 130 of the lower portion 126 may be set by locking the flared handle end 210 into the inner diameter of the hub 142. Further, the electrocap assembly 104 may be bonded to the hub 142. For example, medical grade adhesive may be applied to the end of the hub 142 to bond the surface of the electrocap assembly 104 to an inner surface of the hub 142, as illustrated in FIG. 9.

Figure 10:
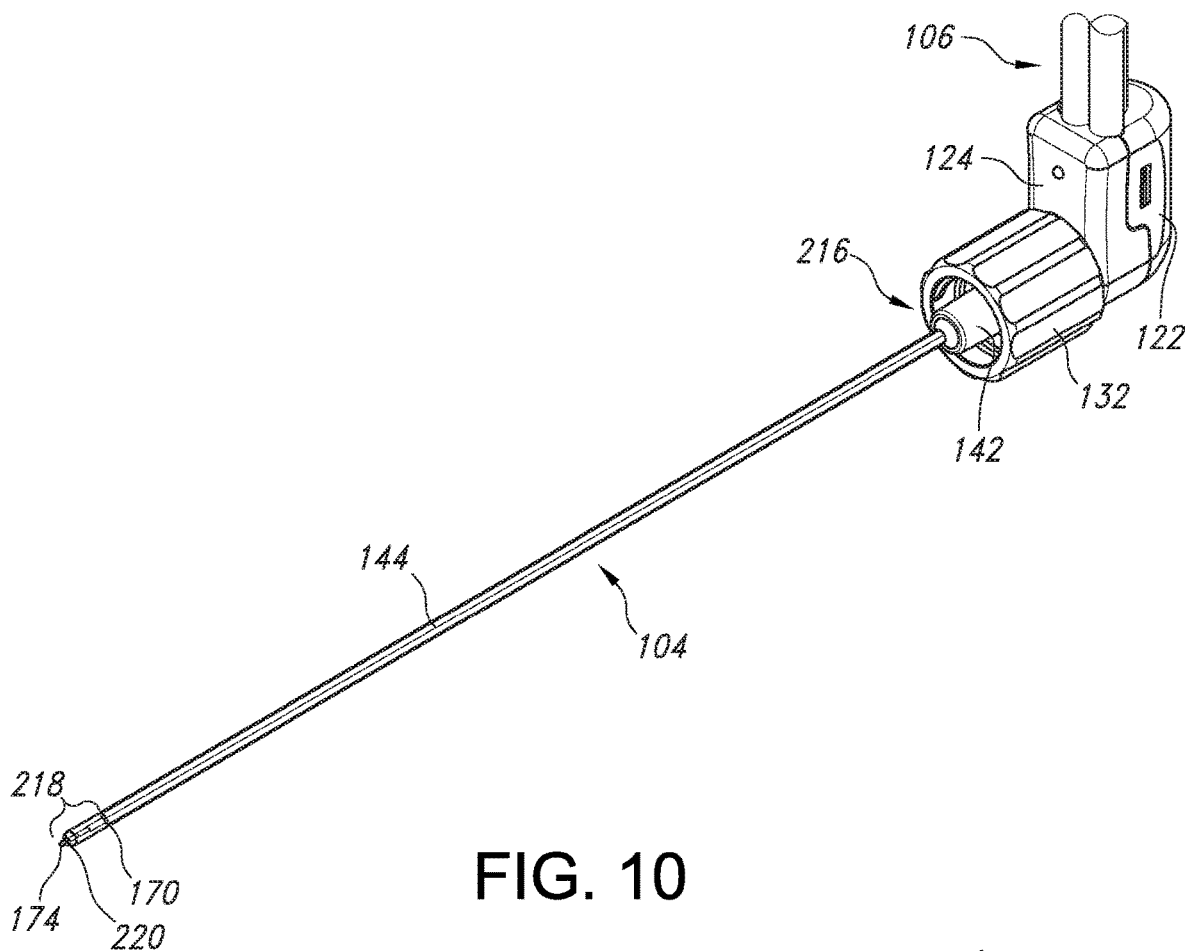
FIG. 10 illustrates a perspective view of the electrocap assembly of the probe of FIG. 3.
Figure 11:
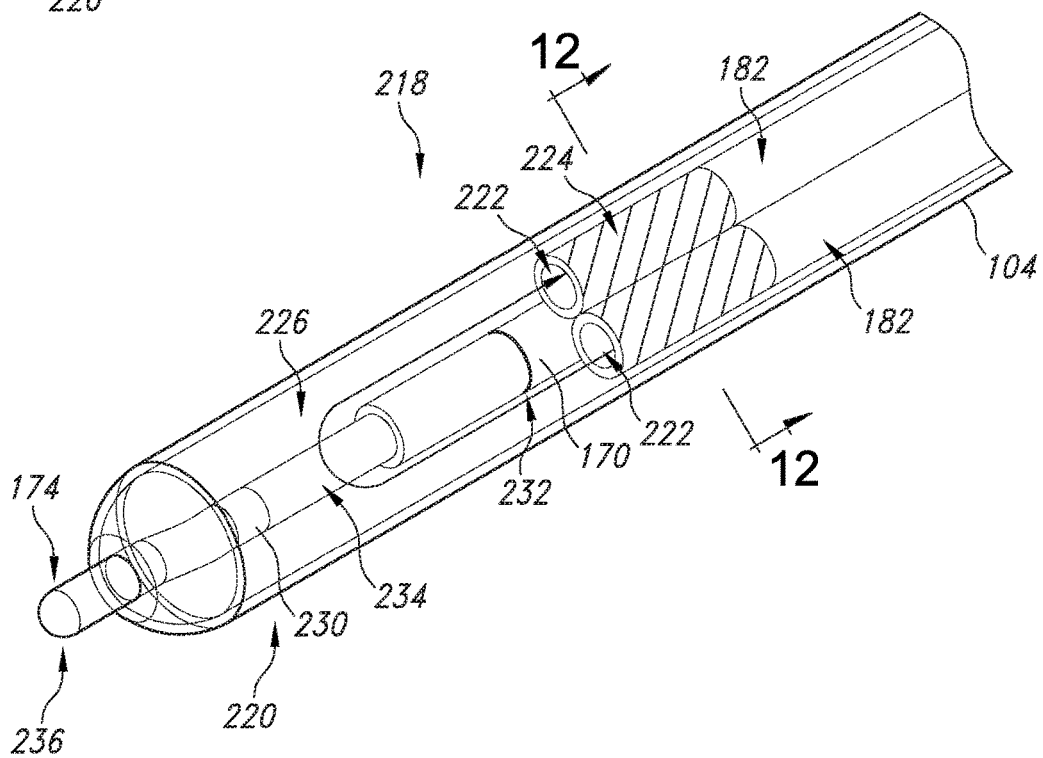
FIG. 11 illustrates a perspective cut-away view of the active tip of the electrocap assembly of FIG. 10.

Referring now to FIGS. 10-11, the electrocap assembly 104 will be described in more detail. As stated above, the electrocap assembly 104 includes a thermocouple hypotube 170 located within the electrocap assembly 104 and extending the length of the electrocap assembly 104. The hypotube 170 may be made from, for example, stainless steel or other suitable material. The constantan wire 174 positioned within the thermocouple hypotube 170 can be electrically isolated by insulation along the entire length of the thermocouple hypotube tube 170. The wire 174 can be welded to the thermocouple hypotube 170 at the distal end 218 of the electrocap assembly 104 to form a thermocouple 236. The thermocouple 236 may function as a temperature sensing element to sense the temperature of the patient's tissue and the temperature of the distal end 218 of the electrocap assembly 104.

Further, as shown particularly in FIGS. 10-11, the thermocouple 236 protrudes beyond the distal end 218 of the electrocap 104. More specifically, as shown, the thermocouple 236 may have a length of less than about 1 millimeter (mm) that extends from a distal end 218 of the electrocap 104. In addition, the length of the thermocouple 236 may be chosen to assist in creating lesions of different sizes. For example, in such embodiments, a user may select one or more probes from a plurality of probes having different lengths based on, e.g. a desired lesion size and/or a desired rate of power delivery based on a treatment procedure type of the tissue. In particular embodiments, the length of the thermocouple 236 may range from about 0.20 mm to about 0.70 mm. In additional embodiments, the thermocouple 236 may also have a different shape or volume. Thus, since an actual lesion size will vary with the lengths of the thermocouple 236, a thermocouple 236 having a longer length can be configured to generate lesions of smaller sizes, whereas a thermocouple 236 having a shorter length can be configured to generate lesions of larger sizes.

Accordingly, varying the length of the thermocouple 236 can control and optimize the size of the lesion for different anatomical locations, for instance creating smaller lesions in regions adjacent to critical structures such as arteries and motor nerves. Thus, the range of lengths of the thermocouple 236 of the present disclosure provide several advantages including for example, the ability to create custom lesion volumes for different procedures (i.e. the control of the lesion volume is intrinsic to the mechanical design of the probe, which is independent of the generator and algorithms). As such, existing equipment and settings can be used. In addition, the protrusion distance can be optimized to provide maximum energy output while minimizing rising impedance and power roll-off conditions. Moreover, the different lengths of the thermocouple 236 creates a mechanical safety mechanism to prevent over-ablation in sensitive anatomical regions.

In addition, the length of the thermocouple 236 is configured to increase (or decrease) a power demand of the electrocap 104. Further, as shown, whereby the thermocouple 236 includes a stainless steel hypotube 170, the hypotube 170 may be electrically conductive and may be electrically coupled to the electrocap 104. Placing the thermocouple 236 at this location, rather than within a lumen or volume 226 defined by the electrocap 104, is beneficial because it allows the thermocouple 236 to provide a more accurate indication of the temperature of tissue proximate to the electrocap. This is due to the fact that, when extended beyond the electrocap 104, the thermocouple 236 will not be as affected by the cooling fluid flowing within the volume 226 as it would be were it located within volume 226. Thus, in such embodiments, the electrocap assembly 104 includes a protrusion protruding from the distal region 218 of the electrocap assembly 104, whereby the protrusion is a component of the thermocouple 236.

Figure 12:
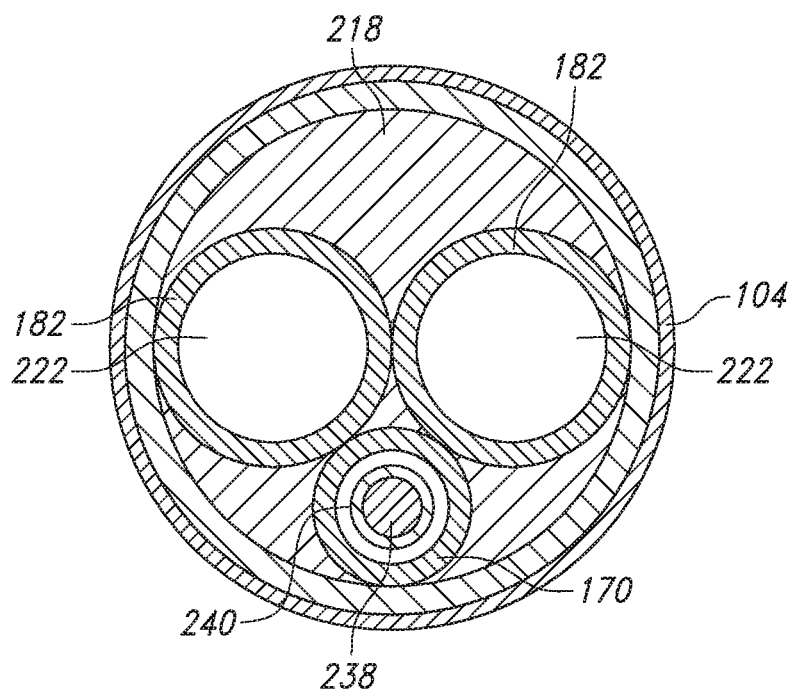
FIG. 12 illustrates a cross-sectional view of the active tip of FIG. 11 taken along line 12-12.

Referring still to FIGS. 10-12, additionally located within the electrocap assembly 104 are two metal fluid tubes 182 which are configured to carry cooling fluid into and out of the distal end 218 of the electrocap assembly 104. The two metal fluid tubes 182 are bonded to the dual-lumen fluid tubing 114 using connecting means (not shown) to form a fluid-tight seal. The connecting means can be any means of connecting two tubes including but not limited to ultraviolet (UV) glue, epoxy or any other adhesive as well as friction or compression fitting. For example, the tubes 182 may be bonded to the dual-lumen fluid tubing by medical grade adhesives (not shown). The two metal fluid tubes 182 may be bent at an angle to approximate the angle 130 of the handle 102, such as about 90 degrees. Both the hypotube 170 containing the constantan wire 174 and the two metal fluid tubes 182 may be inserted or threaded into the electrocap 104. No soldering, welding or other form of bonding is required between the hypotube 170 and the metal fluid tubes 182 within the electrocap assembly 104.

Referring to FIG. 11, the distal end 218 of the electrocap assembly 104 includes a cooled volume 226 inside the electrocap assembly 104 and an active tip 220 for providing the cooled RF treatment to a patient's tissue. The cooled volume 226 is formed by the space between the distal tip 220 and the distal openings 222 of metal fluid tubing 182 within the electrocap assembly 104. As shown in FIG. 11, the cooled fluid flows into the volume 226 towards the distal tip 220 via one of the metal tubes 182 and then back out of the volume 226 through the other of the metal tubes 182. The distal end 130 of the thermocouple hypotube 170 extends a distance 134 beyond the openings 222 of the metal fluid tubing 182. As described above, the thermocouple hypotube 170 protrudes from the distal tip 220 of the electrocap 104, terminating in the thermocouple 236, by which the cooled RF treatment is applied to the patient's tissue. FIG. 12 illustrates a cross-sectional view of the distal end 218 of the electrocap assembly 104, including metal fluid tubing 182 and the portion 238 of constantan wire 174, encapsulated by insulation 240, extending within the distal end 230 of the thermocouple hypotube 170.

Referring still to FIG. 11, in some embodiments, the metal fluid tubing 182 and/or the hypotube 170 may also include a radiopaque marker incorporated somewhere along the length of the metal fluid tubing 182 or hypotube 170. For example, an optimal location for a radiopaque marker may be at or proximate to the distal tip region 218. The metal fluid tubing 182 can have a radiopaque marker 222, and the distal end 230 of the hypotube 170 can have a radiopaque marker 232. The radiopaque markers are visible on fluoroscopic x-ray images and can be used as visual aids when attempting to place devices accurately within a patient's body. These markers can be made of many different materials, as long as they possess sufficient radiopacity. Suitable materials include, but are not limited to silver, gold, platinum and other high-density metals as well as radiopaque polymeric compounds. Various methods for incorporating radiopaque markers into or onto medical devices may be used, such as electroplating, and the present invention is not limited in this regard.

The electrocap assembly 104 can be provided in a variety of lengths such that the probe of the present invention can be used for treatment of different anatomical parts of the body, e.g. the knee joint, the spine, the hip, or other body parts having chronic nerve pain. For example, the electrocap assembly 104 can be provided in lengths sufficient to extend at a particular distance outside of the handle 102, for example about 30 mm, about 50 mm, about 75 mm, about 100 mm, about 150 mm, or other suitable length.

Turning back now to FIGS. 3-4 and 13-15, the structure of the handle 102 will be described in detail. The upper portion 128 of the handle 102 can be formed by an upper shell 122, and the lower portion 126 of the handle 102 can be formed by a lower shell 124. The upper shell 122 and the lower shell 124 may be reversibly mated together. The upper shell 122 and the lower shell 124 may each be formed by molding. An inner perimeter of the upper shell 122 may form a mating surface 190 for contacting a mating surface 192 formed on an outer perimeter of the lower shell 124. In one embodiment, the upper shell 122 may include flex wings 202 on each side lateral side of the upper shell 122, wherein the flex wings 202 extend lower in a direction toward the lower shell 124 than the rest of the upper shell 122. In such configuration, the lower shell 124 includes a corresponding indentation on its lateral sides in which the flex wings 202 are configured to fit with the lower shell 124 at lower mating interface 206. The remainder of the mating surface between the upper shell 122 and the lower shell 124 not including the flex wings 202 forms an upper mating interface 204.

Turning to FIGS. 6A-6B and 13-15, in one embodiment, the upper shell 122 and lower shell 124 are reversibly mated together by a snap engagement. The snap may be formed by at least one cantilever snap 134 extending from the lower shell 124 toward the upper shell 122. The cantilever snap 134 may include a snap sliding surface 136 which is configured to slide against the mating surface 190 of the upper shell 122 and a snap locking surface 138 which is configured to lock in place in a corresponding slot 140 on a lateral side wall of the upper shell 122. The snap engagement may be formed by a single snap and slot or by a plurality of corresponding snaps and slots on the upper 122 and lower 124 shells, respectively. The at least one slot 140 in the upper shell 122 may be positioned on a flex wing 202 of the upper shell 122. However, it is contemplated that alternative locking means for reversibly mating the upper shell 122 and lower shell 124 can be used.

Figure 13:
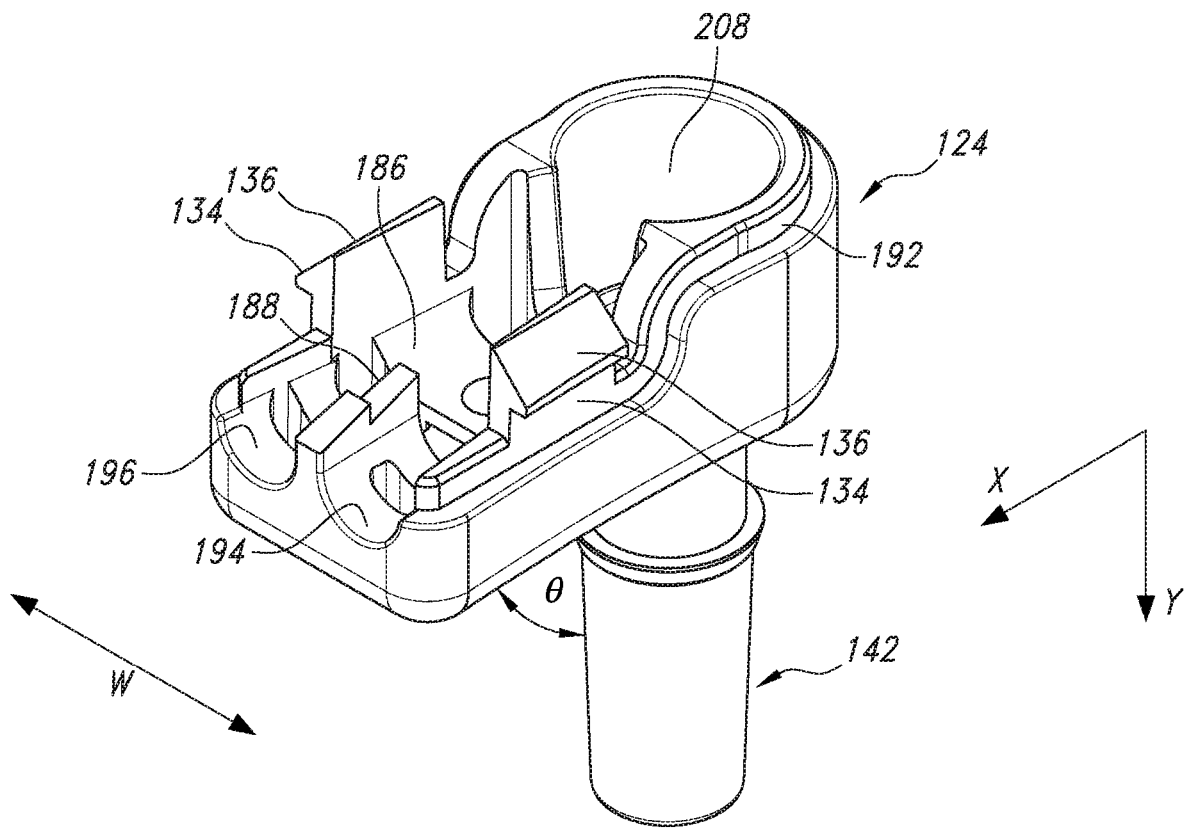
FIG. 13 illustrates a perspective view of a lower shell of the probe handle of FIG. 3.
Figure 14:
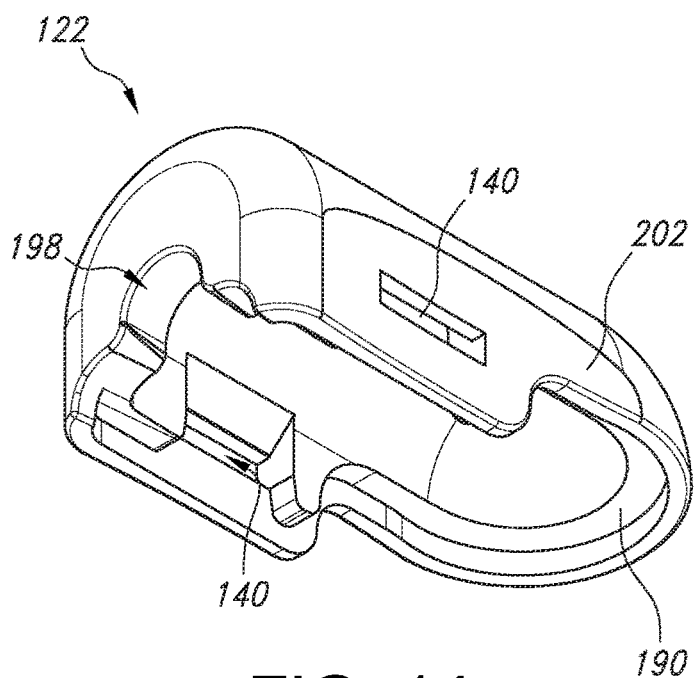
FIG. 14 illustrates a perspective view of an upper shell of the probe handle of FIG. 3.
Figure 15:
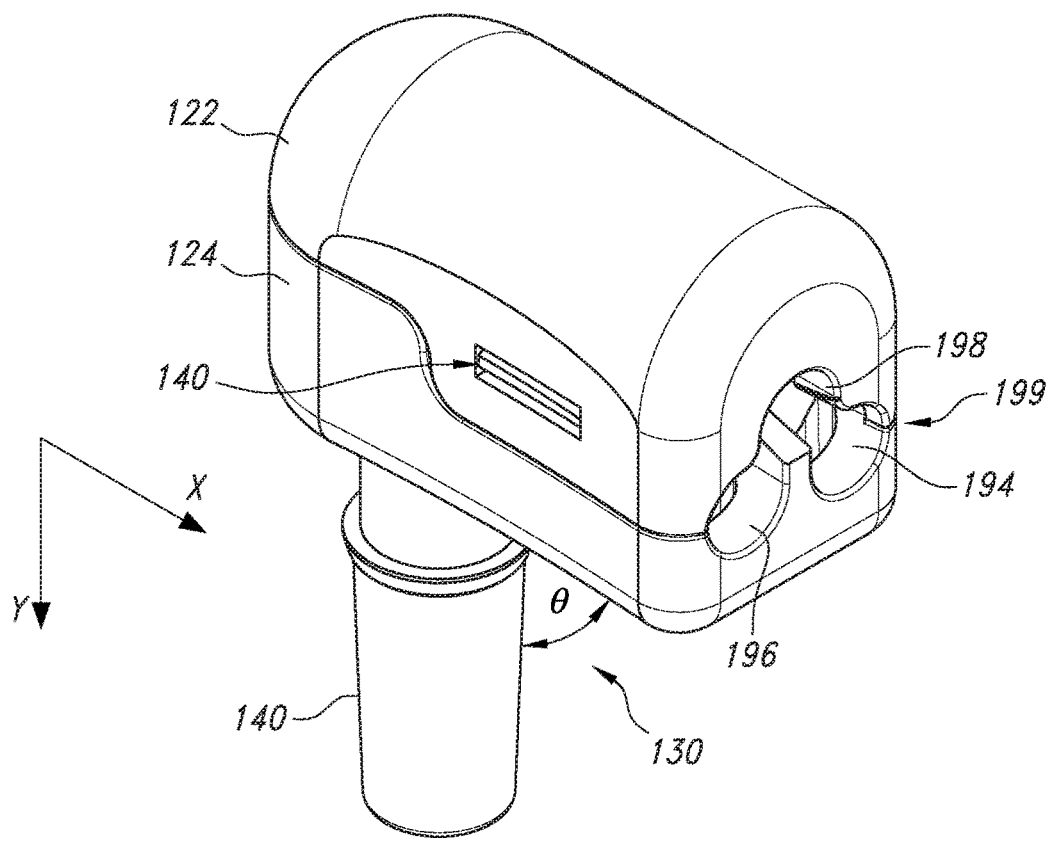
FIG. 15 illustrates the probe handle of FIG. 3 with the upper shell and lower shell mated together.

As shown in FIGS. 13-15, the handle 102 may include openings for receiving the cable-tubing assembly 106 at a proximal surface 199 of the handle 102. For example, the lower shell 124 may include a first fluid tubing opening 194 and a second fluid tubing opening 196 for receiving each of the lumens 115 and 117 of the dual-lumen fluid tubing 114, and the upper shell 122 may include a cable opening 198 for receiving the electrical cable 110. However, in another embodiment, the openings 194, 196 and 198 may be positioned in any configuration with respect to their positioning on the upper 122 and/or lower 124 shells.

Referring to FIG. 13, in the interior of the handle 102, the dual-lumen fluid tubing 114 may rest in place in a tubing alignment shelf 186. Further, the electrical cable 110 may rest in place inside the handle 102 with a cable grip 188. In one embodiment, the tubing alignment shelf 186 and cable grip 188 are formed in the lower shell 124 of the handle 102. However, in alternate embodiments, these features may be instead incorporated into the upper shell 122 of the handle 102.

Referring now to FIGS. 3, 13 and 15, as described above, the lower shell 124 of the handle 102 can include a protrusion 130 having a hub 142 for holding the electrocap assembly 104. The hub 142 of the protrusion 130 can extend at an angle θ in a range from greater than about 0 degrees and less than about 180 degrees relative to a longitudinal x direction. The cable-tubing assembly 106 can extend in a direction generally parallel to the longitudinal x direction when the electrical cable 110 and dual-lumen fluid tubing 114 are seated within openings 194, 196 and 198 of the handle 102, i.e. the longitudinal x direction. The angle θ can be in a range from about 45 degrees to about 135 degrees, such as from about 60 degrees to about 120 degrees. In one embodiment, the angle θ can be about 90 degrees to form a generally perpendicular angle with respect to the longitudinal x axis. Thus, the extended electrocap assembly 104 can extend from the hub 142 in a transverse y direction generally perpendicular to the longitudinal x direction that the cable-tubing assembly 106 extends from the handle 102. In this manner, the moment arm of the probe assembly 100 can be reduced as compared to that of the prior art probe 10 of FIGS. 1 and 2.

Figure 2:
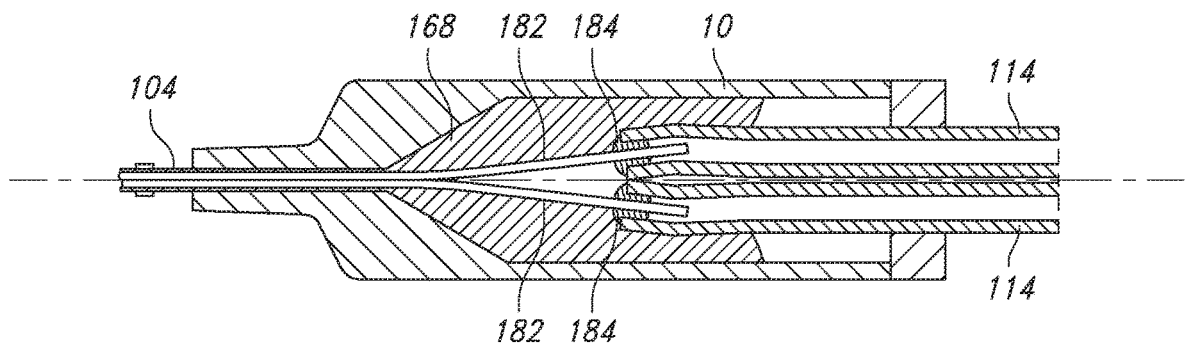
FIG. 2 illustrates a cross-sectional view of the prior art probe handle of FIG. 1 taken along the line 2-2.

Furthermore, the probe 100 of the present invention can have significantly reduced dimensions and overall mass as compared to the prior art probe 10 of FIGS. 1-2. For example, the upper shell 122 of the handle 102 can have a length $L_1$, as shown in FIG. 4, in a range from about 0.5 inches (12.7 mm) to about 1.5 inches (38.1 mm), such as from about 0.6 inches (15.24 mm) to about 1 inch (25.4 mm), such as about 0.7 inches (17.78 mm) to about 0.75 inches (19.05 mm). The handle 102 can have a total height $L_2$, including the upper shell 122 and lower shell 124 having the hub 142, in a range from about 0.75 inches (19.05 mm) to about 1.75 inches (44.45 mm), such as from about 0.9 inches (22.86 mm) to about 1.25 inches (31.75 mm), for example from about 0.95 inches (24.13 mm) to about 1 inch (25.4 mm). The handle 102 can have a height $L_3$, including the upper shell 122 and lower shell 124 but excluding the hub 142, in a range from about 0.25 inches (6.35 mm) to about 0.75 inches (19.05 mm), such as from about 0.35 inches (8.89 mm) to about 0.65 inches (16.51 mm), for example from about 0.4 inches (10.16 mm) to about 0.5 inches (12.7 mm). The handle 102 can have a width W as shown in FIG. 13 in a range from about 0.2 inches (5.08 mm) to about 0.5 inches (12.7 mm), such as from about 0.3 inches (7.62 mm) to about 0.4 inches (10.16 mm), for example about 0.35 inches (8.89 mm). The probe 100 of the present invention can have a mass in a range from about 25 grams to about 35 grams, such as from 28 grams to 34 grams, for example from about 30 grams to about grams.

In comparison, the prior art probe 10 of FIGS. 1-2, which has a handle with an extended cylindrical shape, is significantly longer and heavier than the probe 100 of the present invention. The prior art probe 10 can have a cylindrical axial length in a range from about 1.5 inches to about 2.5 inches, and a diameter in a range from about 0.4 inches to about 0.7 inches. The prior art probe 10 has a mass of about 45 grams. Thus, the probe 100 of the present invention has about 30% reduction in mass as compared to the prior art probe 10. Further, the extended cylindrical shape of the handle of the prior art probe 10 has a significantly greater moment arm when inserted into the patient's tissue due to the electrical cable and fluid tubing extending along a same axis as the cylindrical handle and the electrocap assembly 104 (as illustrated in FIGS. 1-2). Thus, due to the smaller dimensional size, mass, and angled shape of the handle 102 of the probe 100 of the present invention, the probe 100 can result in significantly easier maneuverability and handling by a physician and reduced trauma to patient's tissue from the insertion or movement of the probe 100.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A probe for delivering electrical and thermal energy to tissue of a patient's body, the probe comprising:
   a handle having an upper portion formed by an upper shell and a lower portion formed by a lower shell, the upper portion and the lower portion generally extending in a longitudinal direction, the upper portion and the lower portion removably coupled along a coupling surface such that the upper portion and the lower portion can be separated;
   an extended electrocap assembly interfacing, at a proximal end of the extended electrocap assembly, with one end of the handle, the extended electrocap assembly extending transverse to at least a portion of the coupling surface of the upper and lower portions, the extended electrocap assembly comprising:
      an elongated tube extending from the handle to a distal end that is opposite from the proximal end; and
      a thermocouple hypotube extending from the handle to the distal end and internally to the elongate tube;
   a cable-tubing assembly interfacing with another end of the handle, the cable-tubing assembly comprising an electrical cable having two or more wires and a dual-lumen fluid tubing that terminates within the handle, wherein the cable-tubing assembly extends from the handle at a first angle of greater than 0 degrees and less than 180 degrees relative to the extended electrocap assembly;
   two fluid-carrying tubes mechanically bonded to and extending from respective lumens of the dual-lumen fluid tubing, the two fluid-carrying tubes extending through the handle, internal to and along a length of the elongated tube, and to a cooled volume at the distal end of the extended electrocap assembly, wherein:
      the cooled volume is defined as a space between respective distal openings of the two fluid-carrying tubes within the electrocap assembly and the distal end of the extended electrocap assembly; and
      the two fluid-carrying tubes are bent within the handle in a continuous manner and extend from respective ends of the dual-lumen fluid tubing and into the elongated tube, such that a portion of each of the two fluid-carrying tubes extends internal to and along the length of the elongated tube is at a second angle relative to the cable-tubing assembly; and
   a mechanical clip positioned within the handle and at the second angle relative to the cable-tubing assembly, wherein:
      the mechanical clip mechanically interfaces with one end of the thermocouple hypotube by clipping about at least a portion of a circumference of the thermocouple hypotube to hold the thermocouple hypotube at the second angle relative to the cable-tubing assembly; and
      at least one wire of the electrical cable is electrically and mechanically coupled to the mechanical clip via a solder connection, thereby electrically coupling the thermocouple hypotube to the at least one wire when the thermocouple hypotube is retained by the mechanical clip.

2. The probe of claim 1, wherein the handle forms a housing for electrical connection between the extended electrocap assembly and the electrical cable.

3. The probe of claim 1, wherein at least a portion of the mechanical clip is secured about a circumference of the hypotube.

4. The probe of claim 1, wherein the handle forms a housing for fluid connection between the extended electrocap assembly and the dual-lumen fluid tubing.

5. The probe of claim 1, wherein the lower portion comprises a protrusion extending at an angle with respect to the longitudinal direction, wherein the extended electrocap assembly extends from the protrusion.

6. The probe of claim 5, wherein the first angle and the second angle range from 45 degrees to 135 degrees.

7. The probe of claim 5, wherein the protrusion is generally perpendicular to the longitudinal direction.

8. The probe of claim 1, wherein the upper portion of the handle comprises an upper shell, the lower portion of the handle comprises a lower shell, and the upper shell and lower shell are removably mated.

9. The probe of claim 8, wherein the removable mating between the upper shell and the lower shell is configured to lock the upper shell and the lower shell together, wherein at least one of the upper and lower shells form an electrical cable opening and a fluid tubing opening for receiving the electrical cable and the fluid cable, respectively, the electrical cable opening and the fluid tubing opening each defining a curved surface extending from the another end of the handle towards the one end of the handle such that a longitudinal axis of each of the curved surface extends parallel with a corresponding longitudinal axis of the electrical cable and the fluid cable.

10. The probe of claim 8, wherein the removable mating between the upper shell and the lower shell comprises at least one cantilevered snap on the lower shell configured to lock into a slot on the upper shell.

11. The probe of claim 8, wherein an inner perimeter of the upper shell forms the coupling surface with an outer perimeter of the lower shell, and at least a portion of the coupling surface extends generally parallel to the longitudinal direction of the handle.

12. The probe of claim 1, wherein the electrocap assembly comprises a handle end, and a distal end away from the handle, wherein the distal end forms an active tip for delivering electrical and thermal energy to tissue of the patient's body.

13. The probe of claim 12, wherein the handle end of the electrocap assembly is configured to be positioned within the handle and to protrude from a hub of the handle.

14. The probe of claim 12, wherein the distal end of the electrocap assembly extends in a direction generally perpendicular to the cable-tubing assembly.

15. The probe of claim 12, wherein a connection between a flared end of the handle end of the electrocap assembly and the handle sets the length of an elongate member of the electrocap assembly extending from the handle.

16. The probe of claim 12, wherein the handle end of the electrocap assembly is flared.

17. The probe of claim 12, wherein an interference fit secures the handle end of the electrocap assembly.

18. The probe of claim 12, wherein the active tip is electrically and thermally conductive.

19. The probe of claim 1, wherein the thermocouple hypotube is operable to transmit energy from the electrical cable to an active tip of the probe, wherein the active tip comprises a thermocouple to deliver electrical or radiofrequency energy to the patient tissue.

20. The probe of claim 19, wherein the thermocouple protrudes from a tip end of the extended electrocap.

21. The probe of claim 1, wherein the electrical cable and the dual-lumen fluid tubing are bonded together along at least a portion of the length of the cable-tubing assembly.

22. The probe of claim 21, wherein the electrical cable and the dual-lumen fluid tubing are not bonded at an end of the cable-tubing assembly adjacent to the electrical connector and fluid inlet and outlet connectors.

* * * * *